(12) United States Patent
Reid et al.

(10) Patent No.: US 7,758,894 B2
(45) Date of Patent: Jul. 20, 2010

(54) MODIFIED ELAPID VENOMS AS STIMULATORS OF THE IMMUNE REACTION

(75) Inventors: Paul F. Reid, Plantation, FL (US); Laurence N. Raymond, Plantation, FL (US)

(73) Assignee: Receptopharm, Inc., Plantation, FL (US)

( * ) Notice: Subject to any disclaimer, the term of this patent is extended or adjusted under 35 U.S.C. 154(b) by 309 days.

(21) Appl. No.: 11/592,896

(22) Filed: Nov. 6, 2006

(65) Prior Publication Data

US 2008/0107752 A1   May 8, 2008

(51) Int. Cl.
*A61K 35/58* (2006.01)
*A61K 38/17* (2006.01)

(52) U.S. Cl. ......................................... 424/542; 514/12
(58) Field of Classification Search ................. 424/542; 514/12
See application file for complete search history.

(56) References Cited

U.S. PATENT DOCUMENTS 4,341,762 A * 7/1982 Haast ....................... 424/184.1
2003/0211465 A1 * 11/2003 Mundschenk et al. .......... 435/5
2006/0088858 A1 * 4/2006 Reid et al. ..................... 435/6

OTHER PUBLICATIONS

Rosser, "Common questions about the common cold," Canadian Family Physician, Oct. 1974, pp. 113, 115 and 117.*

* cited by examiner

*Primary Examiner*—Karen Cochrane Carlson
*Assistant Examiner*—Rosanne Kosson
(74) *Attorney, Agent, or Firm*—McLaren Legal Services; Margaret J. McLaren

(57) ABSTRACT

Detoxified cobra venom and its constituent neurotoxins have been reported to have potent antiviral activity. Others have reported that snake venoms were generally immune stimulants. Recent research has revealed more specific details on the effects of detoxified venoms and isolated alpha-neurotoxins on cells of the immune system. Exposure of the immune cells to these detoxified proteins yields a strong response in the innate immune reaction that represents the immune systems initial response to infectious agents. Of particular relevance is the marked increase in the expression of genes associated with the production of gamma interferon, a potent antiviral agent and regulator of the immune response. The ability to induce this strong innate response has significant application to those with weakened immune systems where their ability to fight infection has been compromised. It also has the potential application to act as a method to protect individuals from contagious infectious agents as a substitute for anti-viral vaccines.

14 Claims, No Drawings

MODIFIED ELAPID VENOMS AS STIMULATORS OF THE IMMUNE REACTION

BACKGROUND OF THE INVENTION

1. Field of the Invention

The present invention relates to a class of proteins, and a method for stimulating the immune system, especially to the prevention and treatment of diseases such as viral, bacterial and parasitic infections through the stimulation of the innate immune system reaction. The composition is comprised of a modified elapid venoms containing anticholinergic alpha-neurotoxins.

2. Description of the Prior Art

Sanders et al. had commenced investigating the application of modified venoms to the treatment of Amyotrophic Lateral Sclerosis (ALS) in 1953 having employed poliomyelitis infection in monkeys as a model. Others antiviral studies had reported inhibition of pseudorabies (a herpesvirus) and Semliki Forest virus (alpha-virus). See Sanders' U.S. Pat. Nos. 3,888,977, 4,126,676, and 4,162,303. Sanders justified the pursuit of this line of research through reference to the studies of Lamb and Hunter (1904) though it is believed that the original idea was postulated by Haast. See Haast U.S. Pat. Nos. 4,341,762 and 4,741,902. A basis of Sanders' invention was the discovery that such neurotropic snake venom, in an essentially non-toxic state, also could block or interfere with invading pathogenic bacteria, viruses or proteins with potentially deleterious functions. Thus, the snake venom used in producing the composition was a neurotoxic venom, i.e., causing death through neuromuscular blockade. As the dosages of venom required to block the nerve cell receptors would have been far more than sufficient to quickly kill the patient, it was imperative that the venom be detoxified. The detoxified but undenatured venom was referred to as being neurotropic. The venom was preferably detoxified in the mildest and most gentle manner. While various detoxification procedures were known then to the art, such as treatment with formaldehyde, fluorescein dyes, ultraviolet light, ozone or heat, it was preferred that gentle oxygenation at relatively low temperatures be practiced, although the particular detoxification procedure was not defined as critical. Sanders employed a modified Boquet detoxification procedure using hydrogen peroxide (Boquet 1941), outlined below. The acceptability of any particular detoxification procedure was tested by the classical Semliki Forest virus test, as taught by Sanders, U.S. Pat. No. 4,162,303.

In patents issued to Haast, it was suggested that a combination of neurotoxins and an unknown component of viperid venom were required. (Sanders did not employ a viperid venom component). Haast employed native, unmodified venom fractions the administration of which was reported to cause quite extensive pain for 1-2 days post administration resulting often in short therapeutic periods even if the reported effects were quite dramatic. Vague claims to stimulating the immune system were made without a clear mechanism, relating that a strong reaction to the injection of the venom mixture was indicative of a good therapeutic response.

The production of drug product by Dr. M. Sanders was achieved using hydrogen peroxide as the oxidizing agent in addition to other components giving rise to the recipe he employed for over 30 years (Sanders et al., 1975, 1978). This method was patented and published by Sanders on several occasions with the last patent expiring in 1994. Furthermore, several techniques have been developed for modifying neurotoxins. These have included hydrogen peroxide, ozone, performic acid, iodoacetamide and iodoacetic acid. Some of these procedures have been published and others patented. Obviously some procedures are easier than others to utilize and the focus for commercial production has been on the simpler methods.

Literature references of interest are: Boquet P.; Ann. Inst. Pasteur 66:379-396 (1941), Chang C. C., Kawata Y., Sakiyama F. and Hayashi K.; Eur. J. Biochem. 193:L567-572 (1990), Hudson R A, Montgomery I N and Rauch H C. Mol Immunol. (1983) February; 20(2):229-32; Lamb, G and Hunter, W. K, The Lancet, 1: 20-22; Miller, K., Miller, G. G., Sanders, M. and Fellowes, O. N., Biophys et Biophysica Acta 496:192-196) (1977); Sanders M. and Fellows O.; Cancer Cytology 15:34-40 (1975), Yourist, J. E., Haines, H. G. and Miller, K. D. (1983) J. Gen Virol., 64, 1475-1481

SUMMARY OF THE INVENTION

It is a principal object of the invention to provide a method for preventing and treating infectious diseases, such as colds and flu, bacterial and parasitic infections and the like.

It is a further object of the invention to provide a therapy for the relief of diseases of the aforementioned type, which therapy is safe, effective and may be administered over long periods of time.

Other objects will be apparent to those skilled in the art from the following disclosures and appended claims.

The present invention accomplishes the above-stated objectives, as well as others, as may be determined by a fair reading and interpretation of the entire specification.

In accordance with a principal aspect of the present invention a modified and detoxified cobra venom and neurotoxins purified therefrom suitably detoxified can prevent the onset and suppress the continued development of infections in healthy individuals.

DETAILED DESCRIPTION OF THE PREFERRED EMBODIMENTS

As required, detailed embodiments of the present invention are disclosed herein; however, it is to be understood that the disclosed embodiments are merely exemplary of the invention which may be embodied in various forms. Therefore, specific functional details disclosed herein are not to be interpreted as limiting, but merely as a basis for the claims to be later appended and as a representative basis for teaching one skilled in the art to variously employ the present invention in virtually any appropriate circumstance.

Cobra venoms are characterized by their neurotoxic activity which is a result of one or more neurotoxins found within the venom. Alpha-cobratoxin is an anticholinergic neurotoxin (alpha-neurotoxin) found in some cobra venoms. In their native state they are an antagonist of the alpha-nicotinic acetylcholine receptor. Other alpha-neurotoxins have been isolated from related species of snakes and fish-eating sea snails (*Conus geographus, textilis, imperialis* and *striatus*). Cobratoxin and alpha-bungarotoxin (elapid, krait) have highest affinity for NAchRs containing the alpha 1 and 7 subunits (for a review, see Lucas, 1995). The toxicity of these molecules is based upon their relative affinity for the receptor which far exceeds that of acetylcholine. Many studies (Sanders et al 1953, Miller et al., 1977, Hudson et al., 1983, Lentz et al., 1987, Donnelly-Roberts and Lentz, 1989, Chang et al., 1990) have demonstrated various methods for the chemical modification of cobratoxin. This is accomplished by oxidation of the cobratoxin with substances such as hydrogen peroxide, formalin and ozone, which results in an alteration in affinity for the acetylcholine receptor (AchR) and a concomitant loss in toxicity.

As taught by Sanders, removal of the toxicity of cobratoxin can be achieved by exposure to heat, formalin, hydrogen peroxide, performic acid, ozone or other oxidizing/reducing agents. The result of exposure of cobratoxin to these agents is the modification of amino acids as well as the possible lysis of one or more disulfide bonds. Tu (1973) has demonstrated that the curaremimetic alpha neurotoxins of cobra and krait venoms lose their toxicity upon either oxidation or reduction and alkylation of the disulfide bonds which has been confirmed by Hudson et al. (1983). Loss of toxicity can be determined by the intraperitoneal injection of excess levels of the modified cobratoxin into mice. In general a 0.5 ml volume containing 0.5-1 mg of modified cobratoxin is tested, which represents a minimum of a 4000-fold reduction of toxicity. Alternatively, loss of toxicity can be evaluated by depression of binding of the modified neurotoxin to acetylcholine receptors (AchR) in vitro. Cobra venoms are a relatively cheap raw material source whose production can be scaled up to meet higher demands. Parenteral, oral and topical formulations of MN and MCTX have been described previously by the above identified authors.

Cobra venom (MN) and cobratoxin (MCTX) in their oxidized (modified or non-toxic) forms have demonstrated antiviral activities in-vitro and in-vivo against poliovirus, pseudorabies virus, Semliki Forest virus, herpes simplex 1 virus, HIV and rabies virus, viruses without any obvious similarities in structure or infectious pathway. Native cobratoxin and formaldehyde-treated cobratoxin reportedly lack this activity (Miller et al., 1977). The mechanism by which MN or MCTX exert this capacity was not clear as many viruses employ a variety cell surface receptors as portals for entry into the cell prior to replication. Hudson et al. (1983) reported that cobratoxin subjected to alkylation would inhibit the onset of experimental acute encephalitis (EAE) in guinea pigs, a model for multiple sclerosis. EAE is a T-cell mediated autoimmune disease. The study was undertaken as sequence homology was noted between cobratoxin and myelin basic protein (MBP), the protein antigen used to induce the disease. Recently, MCTX has been shown to inhibit the replication of the human immunodeficiency virus (HIV) in peripheral blood mononuclear cells (PBMC's) suggesting the ability of the protein to influence events within immune cells. The mechanism of action was unclear save to say that there is no direct effect on the virus and there is an event at the cell surface that renders the cell resistant to viral infection. This conclusion was drawn from the fact the pretreatment of the immune cells with MCTX followed by removal of the drug still results in reduced viral replication (Yourist et al., 1983). This antiviral characteristic is also maintained in cells reportedly devoid of acetylcholine receptors such as baby hamster kidney (BHK-21) cells.

Human T lymphocytes are a major source for acetylcholine (Ach) (Fujii and Kawashima, 2001; Sato et al., 1999; Kawashima et al., 1998; Fujii et al., 1996) suggesting a link between the nervous and immune systems. Messenger RNA expression of subunits for both nAchR (a2-a7 and a2-a4) was identified in human PBMCs indicating the presence of NAchR on the cell surface (Sato et al., 1999). Inhibition of Concanavalin-A (Con A) induced T cell proliferation was blocked by the NAchR's antagonist mecamylamine and counter-intuitively by the agonist nicotine (Singh et al., 2000). Acute nicotine exposure of Con A stimulated mouse splenocytes resulted in decreased production of IL-10 and also resulted in increased production of interferon (IFN)-gamma (Hallquist et al., 2000). Affinity purification T-cell receptors using a-BTX confirmed that the NAchR were the same alpha-neurotoxin-sensitive receptors as those found in muscle (Toyabe et al., 1997). Additionally, binding of $^3$H-nicotine to human neutrophils, monocytes and lymphocytes (Davies et al., 1982) has been reported. The formation of E-rosettes, a function of T cells from peripheral blood, and a method used for T cell enumeration, is decreased by 30%-40% by carbamylcholine chloride, a cholinergic antagonist, confirming the expression of NAchRs on at least one subset of human T cells (Mizuno et al., 1982).

Therefore, T-cell functions can clearly be influenced by anticholinergics including peptide neurotoxins, an important aspect in immunity. Consequently, it was selected to assay the effects of MN and MCTX on the transcription of genes in purified T-cells by micro array analysis to understand the mechanisms associated with immune modulation and antiviral activity. Based on prior anti HIV studies, venoms from the Cape (*Naja nivea*) and Thailand (*Naja kaouthia*) cobra were chosen in addition to detoxified cobratoxin, isolated from the Thailand cobra, to be studied in the micro-array assay. The data revealed the all these products induced an upregulation of the genes encoding cytokines involved in the innate immune reaction. Cytokines such as IL-2, Il-8, Il-18, Il-23 were upregulated in addition to a major increase in genes associated with the expression of interferon gamma and interferon related proteins over normal unexposed T-cells. There were slight differences in the profile of upregulation within those associated genes by the different products.

It is interesting to note that in most cases MCTX induced higher transcription of these immune regulatory genes compared to MN possibly due to a dose related effect (equal doses of each were employed in the studies). MCTX upregulated IFN-gamma and Il-23 most whereas MN from Naja nivea upregulated IL-18 most, which is interesting in light of this MN's higher antiviral activity. However, it emphasizes the important contribution of alpha-neurotoxins to the activity in MN preparations.

The large and consistent induction of interferon gamma provides an explanation for the broad antiviral activity historically associated with these products. Interferons alpha and beta were not upregulated to any significant degree over control cells. These results are also consistent with clinical reports by treated subjects of improved health status and resistance to infections especially of viral origin. The study implies that normal individual exposed to these products will respond through the increased production of innate immunity cytokines such as interferon gamma and thereby adopt an antiviral or heighten immune reactivity to infection. It should be noted that similar studies conducted in PMBCs from subjects with an autoimmune disease yielded a different expression profile, which emphasizes the regulatory pathways involved in gene expression. Therefore one supposes that the products could be employed within the scope of an infection control and prevention strategy such as is currently adopted for flu season in elderly, immune suppressed and infant populations. In addition, they could be employed in a therapeutic role in viral infections or in association with standard treatments for bacterial and parasitic infections to effect a more rapid recovery. In viral infections such as influenza the composition would provide advantages over vaccine-based strategies in that it does not have to be virus or subtype specific and would be readily accessible during outbreaks and pandemics. Moreover the use of these products could be beneficial in subjects suffering from the side effects of cancer therapy through reduced immune reactivity. Furthermore the upregulation of cytokines like IFN-gamma could contribute to the therapeutic response in cancer patients.

It is envisioned that a subject may be given MN or MCTX as infrequently as every other week though it is preferred that the composition be administered at least biweekly. The composition may be administered orally, subcutaneously, intramuscularly or intravenously. Parenterally, either subcutaneous or intramuscular injection is preferred. While the correct formulation with benzalkonium chloride will permit oral administration through absorption through the oral mucosa (preferably sublingually), this formulation may also permit administration otically. Furthermore transdermal delivery may be effected if formulated in an appropriate cream or lotion base using benzalkonium chloride or propylene glycol as a permeation enhancer.

EXAMPLE 1

Micro-Array Analysis of Human T-Cells Exposed to Modified *Naja nivea* Venom (MNN)

Methods: T-cells were collected from waste whole blood collected under IRB-approved protocol. In brief, blood was placed in Becton Dickenson Cell-Prep Tubes (CPT) and centrifuged to separate PBMC's from RBC's. PBMC's were collected, washed 3× with warm PBS and cultured on plastic overnight at 37° C./5% $CO_2$ in RPMI-1640 containing protein and cytokine supplementation to remove macrophages. Remaining PBMC's were again washed 3× with PBS and mixed with DynaBeads. The T-cells were then isolated by magnetic bead separation. The purified T-cells were washed 3× with warm PBS and cultured for 2 days as described above to acclimate the T-cells to culture conditions. T-cell purity was confirmed by flow cytometry.

Assay: 5.0E5 T-cells from each sample were removed from the culture and divided into 2 parallel cultures, one containing 2.5E5 cells with 10 ug/ml of modified venom in 2.5 ml serum/cytokine-free RPMI-1640 and the other containing 2.5E5 cells with 2.5 ml serum/cytokine free medium. Cells were then placed in culture for 18 hours. Using a CASYLTTC Cell Analyzer to determine remaining cell concentration, 1.25E5 cells were harvested, washed 3× with warm PBS-T and centrifuged into a pellet. After removal of the final wash supernatant, the pellet was resuspended in RNA-preservation solution and snap-frozen in liquid nitrogen and stored at −130° C. until Micro-array analysis.

Micro-array Analysis: Samples were transported on dry ice to the microarray facility and processed per standard protocol as established and published by Affymetrix. Briefly, RNA is harvested, placed on HG-U133Plus2.0 array chips. After hybridization, chips were placed into Affymetrix chip reader and analyzed.

Statistics: The control samples cultured in parallel without drug exposure were used to subtract background from the test samples. Once background was subtracted, the individual data were combined and subjected to statistical analysis. The data was reported as the means of the samples that met 90% confidence (p=0.10).

The 11 genes that were upregulated most are reported in Table 1.

EXAMPLE 2

Micro-Array Analysis of Human T-cells Exposed to Modified *Naja kaouthia* Venom (MNK)

Method of analysis was as described for Example 1 and the responses in cytokine production are reported in Table 1.

EXAMPLE 3

Micro-Array Analysis of Human T-Cells Exposed to Modified Cobratoxin (MCTX)

Method of analysis was as described for Example 1 and the responses in cytokine production are reported in Table 1.

Cobratoxin represents 15-20% of *Naja kaouthia* venom and so it could be concluded that the venom results reflect a cobratoxin low-dose response. However, *Naja nivea* venom has very low levels of cobratoxin though it still induces the innate immune response strongly and has strong antiviral activity presumably due to the presence of other alpha-neurotoxins such as cobrotoxin.

TABLE 1

The fold increase in cytokine genes upregulated by MN and MCTX over untreated controls.

| No. | Gene | MNN | MNK | MCTX |
|---|---|---|---|---|
| 1 | Interferon gamma | 11.8 | 6.12 | 23.1 |
| 2 | Interferon inducible protein | 7.09 | 6.16 | 21.18 |
| 3 | Macrophage inflammatory protein | NA* | 5.1 | 12.77 |
| 4 | Il-23 | NA | 5.99 | 14.27 |
| 5 | IL-18 | 5.56 | 2.1 | 2.7 |
| 6 | Il-10 | 2.06 | 1.92 | 3.10 |
| 7 | IL-8 | 1.99 | NA | 4.87 |
| 8 | IL-5 | 2.1 | 2.0 | 0.75 |
| 9 | Il-2 | 1.94 | 3.2 | 3.06 |

*NA = not induced.

While the invention has been described, and disclosed in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method of treating infection by an influenza virus in an animal subject comprising upregulating at least one gene encoding an immune regulatory cytokine in the subject's T-cells by administering to the subject a composition comprising a therapeutically effective amount of a detoxified and neurotropically active oxidized alpha cobratoxin or alpha-cobratoxin protein.

2. The method of claim 1 in which the composition is administered subcutaneously, intramuscularly, or intravenously.

3. The method of claim 2 wherein the composition is administered by subcutaneous or intramuscular injection.

4. The method of claim 1 wherein the subject is a human.

5. The method of claim 1, wherein the immune regulatory cytokine is selected from the group consisting of interleukin-2 (IL-2), IL-8, IL-18, IL-23, interferon gamma (IFN-γ), interferon inducible protein, and macrophage inflammatory protein.

6. The method of claim 1 wherein the protein is alpha-cobratoxin isolated from the venom of *Naja kaouthia*.

7. The method of claim 1, wherein the protein is alpha-cobrotoxin isolated from the venom of *Naja nivea*.

8. A method of inhibiting infection by an influenza virus in an animal subject comprising upregulating at least one gene encoding an immune regulatory cytokine in the subject's T-cells by administering to the subject a composition comprising a therapeutically effective amount of a detoxified and neurotropically active oxidized alpha cobratoxin or alpha-cobrotoxin protein.

9. The method of claim 8 wherein the composition is administered subcutaneously, intramuscularly, or intravenously.

10. The method of claim 9 wherein the composition is administered by subcutaneous or intramuscular injection.

11. The method of claim 8, wherein the animal subject is a human.

12. The method of claim 8, wherein the immune regulatory cytokine is selected from the group consisting of interleukin-2 (IL-2), IL-8, IL-18, IL-23, interferon gamma (IFN-γ), interferon inducible protein, and macrophage inflammatory protein.

13. The method of claim 8, wherein the protein is alpha-cobratoxin isolated from the venom of *Naja kaouthia*.

14. The method of claim 8, wherein the protein is alpha-cobrotoxin isolated from the venom of *Naja nivea*.

* * * * *